(12) United States Patent
Toda et al.

(10) Patent No.: US 6,608,221 B1
(45) Date of Patent: Aug. 19, 2003

(54) PROCESS FOR THE PREPARATION OF (2R)-2-PROPYLOCTANOIC ACID

(75) Inventors: Norikazu Toda, Fukaya (JP); Kaoru Yamaguchi, Fukaya (JP); Youichi Iguchi, Sakai-gun (JP)

(73) Assignees: Ono Pharmaceutical Co., Ltd., Osaka (JP); Tokyo Kasei Kogyo Co., Ltd., Tokyo (JP)

(*) Notice: Subject to any disclaimer, the term of this patent is extended or adjusted under 35 U.S.C. 154(b) by 0 days.

(21) Appl. No.: 09/890,651

(22) PCT Filed: Feb. 17, 2000

(86) PCT No.: PCT/JP00/00900
§ 371 (c)(1),
(2), (4) Date: Sep. 10, 2001

(87) PCT Pub. No.: WO00/48982
PCT Pub. Date: Aug. 24, 2000

(30) Foreign Application Priority Data

Feb. 18, 1999 (JP) .............................. 11-039758

(51) Int. Cl.[7] .................. C07C 51/36; C07C 51/00; C07C 57/02; C07C 53/00; C07B 57/00
(52) U.S. Cl. .................. 554/1; 554/124; 554/141; 562/401; 562/598
(58) Field of Search .................. 562/401, 598; 554/124, 141, 1

(56) References Cited

U.S. PATENT DOCUMENTS

| 3,933,889 A | 1/1976 | Magerlein |
| 6,201,021 B1 | 3/2001 | Ohuchida et al. |

FOREIGN PATENT DOCUMENTS

| EP | 0331078 | 9/1989 |
| EP | 0632008 | 1/1995 |
| EP | 1078921 | 2/2001 |
| JP | 6351354 | 3/1988 |
| JP | 8291106 | 11/1996 |
| JP | 08-291106 A | * 11/1996 |
| WO | 9958513 | 11/1999 |

OTHER PUBLICATIONS

Smith, Organic Synthesis 1994, McGraw–Hill, Inc., New York, pp. 428–437.*
Gostunskaya et al., Russian Document, pp. 4–8 (1967) Statement of Relevance provided in concurrently filed Request for Reconsideration.
Augustine, Robert L. et al. "Heterogeneous Catalysis in Organic Chemistry. 2.[1] A Mechanistic Comparison of Noble–Metal Catalysts in Olefin Hydrogenation", J. Org. Chem., American Chemical Society, pp. 1865–1870 (1984).
Roth, Gregory P. et al. "Asymmetric Addition to Chiral Napthalenes 5. An Approach to the Chlorothricolide System", Tetrahedron, vol. 45, No. 22, pp. 6949–6962 (1989).
Hanson, Robert M., "The Synthetic Methodology of Nonracemic Glycidol and Related 2,3–Epoxy Alcohols", Chemical Reviews, vol. 91, No. 4, pp. 437–475 (Jun. 1991).
Patent Abstracts of Japan, Voil. 1997, No. 03, Mar. 31, 1997.
Copy of Search Report dated Jun. 12, 2002.

* cited by examiner

Primary Examiner—Johann Richter
Assistant Examiner—Paul A. Zucker
(74) Attorney, Agent, or Firm—Stevens, Davis, Miller & Mosher, L.L.P.

(57) ABSTRACT

A process for the preparation of (2R)-2-propyloctanoic acid which is characterized by subjecting (2S)-2-(2-propynyl) octanoic acid or (2S)-2-(2-propenyl)octanoic acid to reduction using platinum on carbon. This process gives (2R)-2-propyloctanoic acid having high optical purity without isomerization.

8 Claims, No Drawings

PROCESS FOR THE PREPARATION OF (2R)-2-PROPYLOCTANOIC ACID

This application is a 371 application of PCT/JP00/00900, having been filed Feb. 17, 2000, claiming priority from JP 11-039758, having been filed Feb. 18, 1999.

TECHNICAL FIELD

This invention relates to a process for the preparation of (2R)-2-propyloctanoic acid. More particularly, this invention relates to a process for the preparation of (2R)-2-propyloctanoic acid, which is characterized by subjecting (2S)-2-(2-propynyl)octanoic acid or (2S)-2-(2-propenyl) octanoic acid to reduction using platinum on carbon as a catalyst.

The optically active (2R)-2-propyloctanoic acid (hereinafter, it is referred to as a present compound) prepared by the present process is useful for the pharmaceuticals.

BACKGROUND ART

For the pharmaceutical, an optical purity of the object compound is important. On an activity of optical isomers, there are some reports on pharmaceutical that one of the isomers is superior to the other on a main action, or one does not have toxicity but the other has severe toxicity. A slight amount of optical impurities causes a dangerous unexpected side effect.

Accordingly, for development of safe pharmaceuticals, it is required to use optically active compound instead of racemate, and an optical purity is required to be almost 100%.

The present compound of the present invention is useful for pharmaceuticals. For example, the racemate of (2R)-2-propyloctanoic acid is described in the Example 7(33) of JP-A-7-316092 (EP 632008) as an agent for treating or preventing neurodegerative diseases derived from functional abnormality of astrocytes.

As a result of further study, it was found that the optically active R-configuration compound has strong activities, and lower toxicity. Accordingly, various studies have been conducted to find a process for obtaining the optically active R-configuration compound effectively.

The process for the preparation of (2R)-2-propyloctanoic acid was described, for example, in JP-A-8-291106, wherein an optically active salt was obtained by optical resolution of racemic 2-(2-propynyl)octanoic acid with optically active amine, and the resulting salt was treated with an acid to afford optically active (2S)-2-(2-propynyl)octanoic acid, and then it was subjected to reduction. Besides, in WO 99/58513, (2R)-2-propyloctanoic acid was prepared by subjecting2S-(2-propenyl)octanoic acid or 2S-(2-propynyl) octanoic acid to reduction.

In the above specifications, it was described that a preferable reduction was a catalytic reduction method, more particularly, it may be carried out in an organic solvent, by using a catalyst (e.g. palladium on carbon, palladium, platinum, platinum oxide, nickel) under an atmosphere of hydrogen at 0–60° C. The example using palladium on carbon was described in both specifications.

However, it was proved that a few percentage of S-configuration compound would be inevitably formed as a by-product through isomerization during the reduction under this condition.

DISCLOSURE OF INVENTION

Energetic investigations have been carried out in order to solve the problem of a production of S-configuration compound as by-product. Accordingly the present inventors have found that there occurs substantially no isomerization and present compound having high optical purity can be obtained by using platinum on carbon instead of palladium on carbon and completed the present invention. That is, by the process of the present invention, there occured almost no isomerization, and highly pure and safe medicaments can be supplied.

The fact that by using platinum on carbon, there happened substantially no isomerization and present compound having high optical purity can be obtained was not known until now, and it is proved for the first time at this study.

(2S)-2-(2-propynyl)octanoic acid and (2S)-2-(2-propenyl)octanoic acid used as a starting material were known compounds, for example, described in WO 99/58513.

In the present invention, the hydrogenation of the starting material may be carried out in an organic solvent (e.g. ethyl acetate, tetrahydrofuran, dioxane, dimethoxyethane, diethyl ether, biphenyl ether, methyl alcohol, ethyl alcohol, isopropyl alcohol, benzene, toluene, xylene, HMPA, dimethylformamide, dimethylimidazolidine, mixture thereof), by using a platinum on carbon under an atmosphere of hydrogen at 0–60° C.

Platinum on carbon used in the present invention is commercially available.

A preferable amount for use is 0.1–20 wt %, more preferably 0.1–10 wt % based on the material.

According to the process of the present invention, there occurs no isomerization and (2R)-2-propyloctanoic acid having high optical purity can be obtained compared to conventional process (wherein, palladium on carbon is used as catalyst).

That is, there happened partial isomerization by the conventional process and the optical purity was decreased, but by the process of the present invention, there occurs substantially no isomerization and present compound having high purity can be obtained.

The following table shows optical purity of the present compound, which prepared by the process of the present invention and a conventional process (comparative example 1 and 2 as described later).

TABLE 1

| The starting material | Reduction method (Catalyst) | Optical purity of the starting material | Optical purity of the present compound |
|---|---|---|---|
| (2S)-2-(2-Propenyl) octanoic acid | The method of the present invention (Platinum on carbon) | 99.8% e.e. | 99.4% e.e. |
|  | Comparative example 1 (Palladium on carbon) | 99.0% e.e. | 95.2% e.e. |
| (2S)-2-(2-Propynyl) octanoic acid | The method of the present invention (Platinum on carbon) | 99.9% e.e. | 99.3% e.e. |
|  | Comparative example 2 (Palladium on carbon) | 99.9% e.e. | 97.1% e.e. |

The above table shows that optical purity of the present compound prepared by the process of present invention keeps high optical purity, but the optical purity of the compound prepared by the process of comparative example is remarkably decreased.

Specifically, optical purity of the present compound prepared by the process of comparative examples is decreased by 3.8% and 2.8% on the basis of the starting material, but the optical purity of the present compound is decreased by only 0.4% and 0.6%, and the optical purity of the present compound remains high.

As mentioned above, keeping the content of the by-product as low as possible has a large significance for pharmaceuticals. From this view point, it is an important achievement that an amount of by-product is decreased and optical purity of the present compound remains high. It was not expected at all that these effects could be obtained by the present invention.

Accordingly, by the process of the present invention, the present compound can be obtained without isomerization, and the present compound has a high optical purity, therefore it is considered that the present process is outstanding.

BEST MODE FOR CARRYING OUT THE INVENTION

Hereinafter, the present invention will be described in detail by examples and comparative examples, but these examples are only illustrative and are not construed as being limited thereto.

Reference Example 1

(2S)-2-(2-propenyl)octanoic acid cyclohexylamine

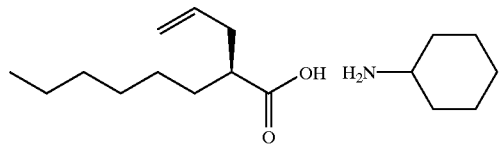

To a solution of N-(2S-(2-propenyl)octanoyl)-(1S)-(−)-2,10-camphorsultam (described in WO 99/58513) (300 g) in dimethoxyethane (DME)(3 L), 2-methyl-2-butene (165 g) and hydrogen peroxide aqueous solution (30%, 177 g) were added at −5∼−10° C. To this solution, a solution of tetra-n-butyl ammonium hydroxide (40% ; 1015 g) in DME (749 ml) was added dropwise over 30 minutes at −10∼0° C. The resulting solution was warmed to 0° C., and stirred for 3 hours. To the reaction mixture, an aqueous solution of sodium sulfite (198.5 g/1050 ml) was added dropwise over 10 minutes, and the mixture was warmed to room temperature, and stirred for 30 minutes. To the mixture, an aqueous solution of hydrochloric acid (1.5 L/water 3 L) was added, and the product was extracted with t-butyl methyl ether (3 L). The organic layer was washed with an aqueous solution of oxalic acid (151 g/water 1.5 L), water (1.5 L×3 times) and a saturated aqueous solution of sodium chloride (2 L), and concentrated. To the concentrated solution, heptane (300 ml) was added and it was concentrated again. To the residue, heptane (600 ml) was added, and an insoluble material was removed by filtration. The filtrate was concentrated, and the residue was dissolved in ethyl acetate (1 L) and cyclohexylamine (70.2 g) with heating, and allowed to stand at ambient temperature over night. The solution was cooled with ice-bath for 1 hour, and the precipitated crystal was collected and dried to give the title compound (145 g; yield 65%).

Reference Example 2

(2S)-2-(2-propenyl)octanoic acid

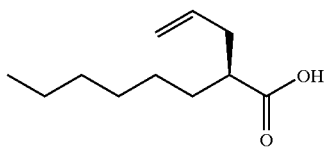

n-Hexane/ethyl acetate (4/1; 2790 ml) and 2N hydrochloric acid (270 ml) were added to the compound prepared in Reference example 1 (140 g), and the mixture was stirred for 30 minutes. The water layer was removed from there action solution, and the organic layer was washed with water (690 ml×3 times), and the product was extracted with 2.6N sodium hydroxide (750 ml). The water layer was washed with n-hexane/ethyl acetate (4/1; 2790 ml×2 times). To the water layer, 2N hydrochloric acid (990 ml) was added, and the product was extracted with n-hexane/ethyl acetate (4/1; 2790 ml). The organic layer was washed with water (690 ml×3 times) and with a saturated aqueous solution of sodium chloride, and concentrated to give the title compound (89 g; yield 98%). Optical purity (measured by gas chromatography): 99.8% e.e.

EXAMPLE 1

Preparation of (2R)-2-propyloctanoic acid Using Platinum on Carbon

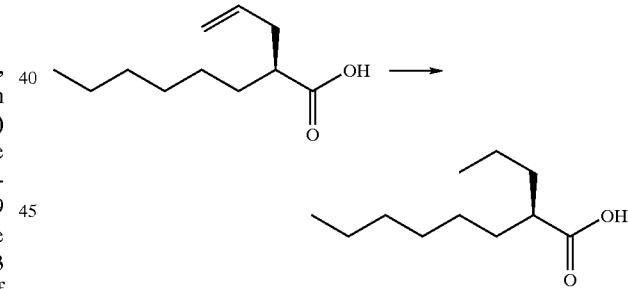

A solution of the compound prepared in Reference example 2 (87 g) in 2-propylalcohol (2.17 L) was added to 5% platinum on carbon (44 wet %) (9.91 g), and the mixture was hydrogenated under a pressure of hydrogen (5 kg/cm²), at 30° C. for 4 hours. The reaction mixture was filtered, and the filtrate was concentrated. To the residue, n-hexane/ethyl acetate (5/1; 1.7 L) was added, and the product was extracted with 2N sodium hydroxide (511 mL). A concentrated hydrochloric acid (86 ml) was added to the water layer, and the product was extracted with n-hexane/ethyl acetate (5/1; 1.7 L). The organic layer was washed with purified water (430 ml×3 times), a saturated aqueous solution of sodium chloride, dried and concentrated. The residue was distilled to give the title compound (75.0 g; yield: 85%) having the following physical data. Optical purity (measured by HPLC): 99.4% e.e.

EXAMPLE 2

Preparation of (2R)-2-propyloctanoic acid Using Platinum on Carbon

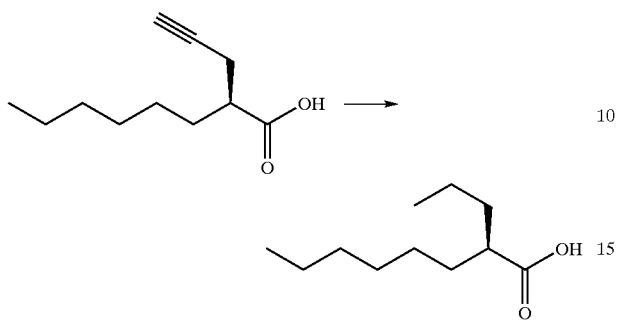

5% Platinum on carbon wet (270 g) was added to a solution of (2S)-2-(2-propynyl)octanoic acid (described in JP-A-8-291106) (43.0 kg; 99.90% e.e.) in isopropylalcohol (344 L), and the mixture was hydrogenated under a pressure of hydrogen (3.9~15.0 kg/cm$^2$), at 20~30° C. for 8 hours. Similarly, 5% platinum on carbon wet (149 g) was added to a solution of (2S)-2-(2-propynyl)octanoic acid (23.7 kg; 99.90% e.e.) in 2-propylalcohol (190 L), and the mixture was hydrogenated under a pressure of hydrogen (2.6~15.0 kg/cm$^2$), at 16~30° C. for 5 hours. A catalyst was removed from the above two reaction solutions. These filtrates were concentrated. The residue was distilled to give the title compound (56.48 kg; yield: 82.8%) having the following physical data. Optical purity (measured by HPLC): 99.34% e.e.

Comparative Example 1

Preparation of (2R)-2-propyloctanoic acid Using Palladium on Carbon

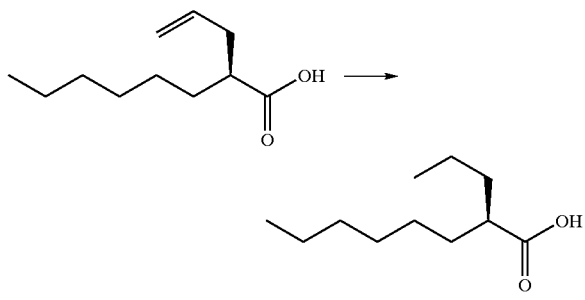

10% Palladium on carbon (17 mg) was added to a solution of (2S)-2-(2-propynyl)octanoic acid (168 mg; 99.0% e.e. (measured by gas chromatography)) in a mixed solution of methanol (1.2 ml) and ethyl acetate (1.2 ml). The mixture was stirred for 1 hour at room temperature under an atmosphere of hydrogen gas. The residue was filtered through Celite (product name), and the filtrate was concentrated. The residue was purified by silica gel column chromatography (hexane:ethyl acetate=9:1→4:1) to give the title compound (109 mg; yield: 65%) having the following physical data. Optical purity (measured by HPLC): 95.2% e.e.

Comparative Example 2

Preparation of (2R)-2-propyloctanoic acid Using Palladium on Carbon

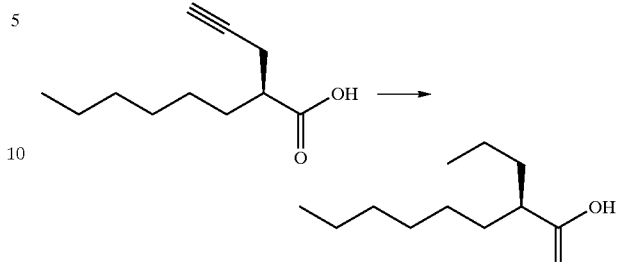

5% Palladium on carbon wet (2.60 kg) and DME (250 kg) were added to a solution of (2S)-2-(2-propynyl)octanoic acid (13.0 kg; 99.88% e.e.) in DME (23.0 kg). The mixture was hydrogenated under a pressure of hydrogen (5.1 m$^3$), at 20~30° C. for 19 hours. The reaction mixture was filtered, and washed with DME (40 L). The filtrate and washing solution was combined and concentrated. The residue was dissolved in n-hexane/ethyl acetate (215 L/43 L), and the product was extracted with 2N sodium hydroxide (72 L). To the exracted water layer, n-hexane/ethyl acetate (215 L/43 L) was added, and the mixture was stirred. A concentrated hydrochloric acid (13 L) was added to the mixture. The organic layer was washed with water (3 times), a saturated aqueous solution of sodium chloride (1 time), dried over anhydrous magnesium sulfate, and concentrated to give a crude title compound (12.25 kg). The crude product was distilled to give the title compound (8399.7 g; yield: 63.2%) having the following physical data. Optical purity (measured by HPLC): 97.14% e.e.

INDUSTRIAL APPLICABILITY

By the process of the present invention, (2R)-2-propyloctanoic acid having high optical purity, which is useful for the pharmaceuticals, can be obtained, and safe medicaments which do not contain by-product causing side effects, can be supplied.

What is claimed is:

1. A process for the preparation of (2R)-2-propyloctanoic acid which is characterized by subjecting (2S)-2-(2-propynyl)octanoic acid or (2S)-2-(2-propenyl)octanoic acid to reduction using platinum on carbon.

2. The process described in claim 1, which is characterized by subjecting (2S)-2-(2-propynyl)octanoic acid to reduction using platinum on carbon.

3. The process described in claim 1, which is characterized by subjecting (2S)-2-(2-propenyl)octanoic acid to reduction using platinum on carbon.

4. (2R)-2-propyloctanoic acid having optical purity greater than 97.14% e.e.

5. The (2R)-2-propyloctanoic acid of claim 4, having optical purity greater than 99% e.e.

6. The (2R)-2-propyloctanoic acid of claim 4, obtained by subjecting one selected from the group consisting of (2S)-2-(2-propynyl) octanoic acid and (2S)-2-(2-propenyl) octanoic acid to reduction using platinum on carbon.

7. The (2R)-2-propyloctanoic acid of claim 4, having an optical purity of at least 99.3% e.e.

8. The (2R)-2-propyloctanoic acid of claim 7, obtained by subjecting one selected from the group consisting of (2S)-2-(2-propynyl) octanoic acid and (2S)-2-(2-propenyl) octanoic acid to reduction using platinum on carbon.

* * * * *